US010598643B2

(12) United States Patent
Green

(10) Patent No.: US 10,598,643 B2
(45) Date of Patent: Mar. 24, 2020

(54) COLORIMETRIC ASSAY FOR MEASURING TYPE I PYRETHROIDS ON TREATED OBJECTS

(71) Applicant: The United States of America, as represented by the Secretary, Department of Health and Human Services, Bethesda, MD (US)

(72) Inventor: Michael D. Green, Winder, GA (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 175 days.

(21) Appl. No.: 15/735,800

(22) PCT Filed: Jun. 10, 2016

(86) PCT No.: PCT/US2016/036935
§ 371 (c)(1),
(2) Date: Dec. 12, 2017

(87) PCT Pub. No.: WO2016/201258
PCT Pub. Date: Dec. 15, 2016

(65) Prior Publication Data
US 2019/0113489 A1  Apr. 18, 2019

Related U.S. Application Data

(60) Provisional application No. 62/174,852, filed on Jun. 12, 2015.

(51) Int. Cl.
*G01N 31/22* (2006.01)
*G01N 21/78* (2006.01)

(52) U.S. Cl.
CPC .............. *G01N 31/22* (2013.01); *G01N 21/78* (2013.01); *Y10T 436/255* (2015.01)

(58) Field of Classification Search
CPC ................... G01N 21/78; G01N 31/22; Y10T 436/173076; Y10T 436/19; Y10T 436/20; Y10T 436/200833; Y10T 436/202499; Y10T 436/25375; Y10T 436/255
USPC ......... 436/63, 110, 124, 127, 128, 130, 164, 436/169, 177, 178; 422/400, 420, 430
See application file for complete search history.

(56) References Cited

U.S. PATENT DOCUMENTS

| 5,278,075 | A | | 1/1994 | Stone | |
|---|---|---|---|---|---|
| 5,723,306 | A | * | 3/1998 | Pullen | ............... C07K 16/44 435/345 |
| 6,896,892 | B2 | * | 5/2005 | Mount | ................ A01N 25/34 424/411 |
| 8,609,428 | B2 | * | 12/2013 | Kaur | .................. G01N 31/22 436/106 |
| 2011/0033945 | A1 | | 2/2011 | Kaur et al. | |

FOREIGN PATENT DOCUMENTS

| JP | 59-166862 A | 9/1984 |
|---|---|---|
| WO | WO 2013/108250 A1 | 7/2013 |
| WO | WO 2016/201258 A1 | 12/2016 |

OTHER PUBLICATIONS

Arip et al., "Reactions of 2,6-dichloroquinone-4-chloroimide (Gibbs reagent) with permethrin—an optical sensor for rapid detection of permethrin in treated wood" *Chemistry Central Journal*, 7: 122-130, 2013.
Enayati et al., "Quantification of pyrethroid insecticides from treated bednets using a mosquito recombinant glutathione S-transferase" *Medical and Veterinary Entomology*, 15(1): 58-63, 2001.
Green et al., "Rapid colorimetric field test to determine levels of deltamethrin on PermaNet® surfaces: association with mosquito bioactivity" *Tropical Medicine and International Health*, 14(4): 381-388, 2009.
Verlé et al., "A simple field test for detecting pyrethroids on impregnated nets" *Tropical Medicine and International Health*, 3(10): 833-836, Oct. 1998.
"Products in Development" (www.americannanofluidics.com/products) (retrieved Mar. 5, 2015) 2 pages.
International Preliminary Report on Patentability, Application No. PCT/US2016/036935, dated Dec. 21, 2017.
International Search Report, Application No. PCT/US2016/036935, dated Aug. 29, 2016.
Written Opinion of the International Searching Authority, Application No. PCT/US2016/036935, dated Aug. 29, 2016.

\* cited by examiner

*Primary Examiner* — Maureen Wallenhorst
(74) *Attorney, Agent, or Firm* — Leydig, Voit & Mayer, Ltd.

(57) ABSTRACT

Disclosed is a method for detecting the presence of a type I pyrethroid in an object including the steps of (a) contacting the object with a solvent and an absorbent substrate, (b) separating the absorbent substrate from the object, (c) evaporating the solvent from the absorbent substrate, (d) treating the absorbent substrate with a solution comprising a nitrite salt in concentrated sulfuric acid, and (e) observing the absorbent substrate for a color change indicating the presence of the type I pyrethroid in the object. The invention also provides a kit for detecting the presence of the type I pyrethroid in an object.

20 Claims, 1 Drawing Sheet

COLORIMETRIC ASSAY FOR MEASURING TYPE I PYRETHROIDS ON TREATED OBJECTS

CROSS REFERENCE TO A RELATED APPLICATION

This patent application is the U.S. national stage of International Patent Application No. PCT/US2016/036935, filed Jun. 10, 2016, which claims the benefit of U.S. Provisional Patent Application No. 62/174,852, filed Jun. 12, 2015, the disclosures of which are incorporated in their entireties by reference for all purposes.

BACKGROUND OF THE INVENTION

Insecticide-treated textiles such as mosquito nets and clothing are commonly used as an intervention in the fight against vector-borne diseases such as malaria, encephalitis, filariasis, leishmaniasis, and West Nile virus. Insecticides frequently used for the treatment of textiles include the pyrethroid class of insecticides, such as permethrin.

Washing of the textiles along with normal wear, particularly in the case of clothing, depletes the insecticide on the material, thereby eventually rendering them ineffective against the insect vectors. Currently, assays for insecticides such as pyrethroids can be provided by complex analytical techniques such as gas chromatography and high performance liquid chromatography (HPLC). Such techniques are well suited for insecticide analysis in production facilities, to assure that desired levels of the insecticides are impregnated into the materials.

However, it would be desirable to quantitatively assay these materials in use in the field to assess the levels of insecticide, and thus effectiveness, so as to avoid the inadvertent exposure of personnel to insect vectors and thus vector-borne diseases. A suitable assay would have to be simple to use and inexpensive to produce. U.S. Patent Application Publication 2011/0033945 A1 discloses a colorimetric assay for the presence of type II pyrethroids, which are a class of pyrethroids containing an alpha cyano ester group obtained by esterification of a cyanohydrin. The assay comprises adding a base and then a mixture of a hydride donor and a hydride acceptor to a sample, and observing the sample for a color change. The assay is based on the detection of cyanide generated from the type II pyrethroid. However, permethrin, which does not contain an alpha cyano ester group, is not detectable in this assay.

In view of the foregoing, an unmet need exists for a simple and reliable quantitative assay of permethrin in textile materials.

BRIEF SUMMARY OF THE INVENTION

The invention provides a method for detecting the presence of a type I pyrethroid in an object comprising the steps of (a) contacting the object with a solvent and an absorbent substrate, (b) separating the absorbent substrate from the object, (c) evaporating the solvent from the absorbent substrate, (d) treating the absorbent substrate with a solution of a nitrite salt in concentrated sulfuric acid, and (e) observing the absorbent substrate for a color change indicating the presence of the type I pyrethroid in the object.

Advantageously, the assay is suitable for implementation under field conditions. Detection and quantitation of type I pyrethroid levels in textiles can be accomplished visually or by using readily available technologies, such as cell phone cameras and image analysis software.

The invention also provides a kit comprising (a) an absorbent substrate, (b) a solvent, (c) a solution of a nitrite salt in concentrated sulfuric acid, (d) at least one sample well, and (e) instructions for use.

BRIEF DESCRIPTION OF THE SEVERAL VIEWS OF THE DRAWING(S)

DETAILED DESCRIPTION OF THE INVENTION

Figure 1:
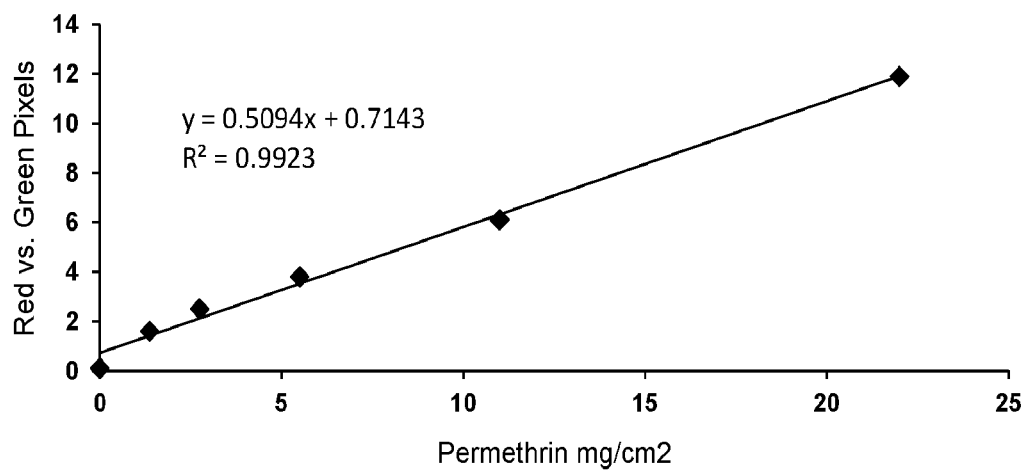
FIG. 1 depicts a calibration curve correlating the ratio of red to green pixels in digital images of samples subjected to the permethrin assay to the concentration of permethrin in the samples, in accordance with an embodiment of the invention.

The invention provides a method for detecting the presence of a type I pyrethroid in an object comprising the steps of (a) contacting the object with a solvent and an absorbent substrate, (b) separating the absorbent substrate from the object, (c) evaporating the solvent from the absorbent substrate, (d) treating the absorbent substrate with a solution of a nitrite salt in concentrated sulfuric acid, and (e) observing the absorbent substrate for a color change indicating the presence of the type I pyrethroid in the object.

The type I pyrethroid can be any suitable type I pyrethroid. Type I pyrethroids are distinguished from type II pyrethroids by not having an alpha cyano group, which is present in type II pyrethroids. Non-limiting examples of type I pyrethroids include allethrin (e.g., S-bioallethrin, D-trans-allethrin, and D-allethin), bifenthrin, esbiothrin, imiprothin, metofluthrin, permethrin, phenothrin, prallethrin, resmethrin, and tetramethrin. In a preferred embodiment, the type I pyrethroid is permethrin.

The object can be any suitable object treated with a type I pyrethroid. For example, the object can be an intact item of clothing or mosquito net. A particularly suitable object is a military uniform treated with a type I pyrethroid and intended for use in tropical regions. For example, the object can be a uniform jacket, uniform pants, or uniform shirt. The object may be made of any suitable material. For example, the object may be made of cotton fibers, polyester fibers, polyamide fibers, polyolefin fibers, polyimide fibers, nylon fibers, or a combination thereof. Preferably, the object is washed prior to assay in order to remove potentially interfering contaminants such as dirt and the like. A portion of the object can be contacted with an absorbent substrate and then contacted with a solvent, such that the solvent dissolves the type I pyrethroid (if present) and is then absorbed by the absorbent substrate. Alternatively, the object can be contacted with a solvent and then contacted with an absorbent substrate. A particular standard area of the object is treated with the solvent to allow for determination of the amount of the type I pyrethroid per unit area of the object. For example, a square area or a circular area of the object can be contacted with the solvent. Use of absorbent substrates having identical dimensions can be used to absorb solvent from an area of the object corresponding to the surface area of the absorbent substrate.

The solvent can be any suitable solvent. Desirably, the solvent is one in which permethrin has a high solubility and which has a boiling point that is high enough to avoid rapid evaporation (such as in tropical climates) but which is low enough to permit ready evaporation. Typically, the solvent has a boiling point in the range of about 60° C. to about 60° C. Non-limiting examples of suitable solvents include acetone, methyl ethyl ketone, methanol, ethanol, isopropanol, ethyl acetate, acetonitrile, dichloroethane, tetrahydrofuran, and cyclohexane. In an embodiment, the solvent comprises acetone or ethanol.

The absorbent substrate can be any suitable substrate. The absorbent substrate can be a glass fiber material, such as a glass fiber filtration disk. In other embodiments, the absorbent substrate can be cloth or a sponge material. When the object is a mosquito net, the absorbent substrate can be lens paper. Desirably, the absorbent substrate is insoluble in the solvent and does not react with the solution of a nitrite salt in concentrated sulfuric acid.

Following contacting the object with the solvent and absorption of the solvent by the absorbent substrate, the solvent is evaporated. The evaporation can be carried out by simple air drying.

The absorbent substrate containing permethrin (if present) is treated with a solution of a nitrite salt in concentrated sulfuric acid. The nitrite salt can be any suitable nitrite salt. Preferably, the nitrite salt comprises a cation that does not react with concentrated sulfuric acid. Non-limiting examples of suitable nitrite salts include alkali nitrite salts such as lithium nitrite, sodium nitrite, potassium nitrite, rubidium nitrite, and cesium nitrite, alkaline earth nitrite salts such as magnesium nitrite, calcium nitrite, strontium nitrite, and barium nitrite, a Group V metal nitrite such as aluminum nitrite, a transition metal nitrite, ammonium nitrite, and combinations thereof. In an embodiment, the nitrite salt is sodium nitrite or potassium nitrite. The solution of a nitrite salt in concentrated sulfuric acid can contain about 1 wt. % to about 50 wt. % of the nitrite salt, for example, about 1 wt. % to about 25 wt. %, about 5 wt. % to about 25 wt. %, about 5 wt. % to about 20 wt. %, or about 5 wt. % to about 15 wt. % of the nitrite salt. A suitable solution of a nitrite salt in concentrated sulfuric acid is the Liebermann reagent, which contains 1 g of potassium nitrite in 10 mL of sulfuric acid. The Liebermann reagent is colorless but turns yellow/orange upon reaction with permethrin.

The treatment of the absorbent substrate can be carried out in any suitable manner. In an embodiment, the treatment is carried out in a sample well of a multi-well sample plate. In this manner, several assays can be carried out simultaneously. The sample well can be an empty sample well or the sample well can contain a carrier material. In an embodiment, the sample well contains a carrier which material desirably forms a reactive gel or a matrix with the solution of a nitrite salt in concentrated sulfuric acid. The carrier material can be any suitable carrier material that desirably does not react with the solution of a nitrite salt in concentrated sulfuric acid. In an embodiment, the absorbent material comprises glass fiber paper. The glass fiber paper can be any suitable glass fiber paper and can be glass fiber filter paper. In a preferred embodiment, the carrier material comprises glass fiber paper impregnated with silica. The carrier material facilitates transportation without leakage and further permits preparation of a multi-well sample plate already containing the carrier material pre-wetted with the solution comprising a nitrite salt.

In an embodiment, the dried absorbent substrate is placed into the sample well and is pressed firmly (e.g., via a glass vial) onto the matrix containing the solution of a nitrite salt in concentrated sulfuric acid. This technique allows for an immediate and consistent distribution of the reagent over the entire absorbent substrate, resulting in an evenly distributed coloration. An orange/red color typically appears immediately. The color is recorded via a camera for subsequent image analysis. After the assay is performed, the sulfuric acid can be neutralized with, e.g., calcium carbonate to allow for safe disposal.

In other embodiments, the dried absorbent substrate is simply treated with the solution of a nitrite salt in concentrated sulfuric acid on a flat surface, to allow the reaction to occur on the dried absorbent substrate.

In an embodiment, the absorbent substrate is lens paper, and the absorbent substrate is treated with sulfuric acid in the absence of a nitrite salt. In the presence of permethrin, a red color is generated.

The amount of type I pyrethroid present in the textile object can be quantitated by measuring the absorbance of the contents of the sample well and then comparing the measured absorbance to a standard calibration curve obtained by analysis of samples containing different amounts of a type I pyrethroid. In an embodiment, a digital image can be analyzed to determine the ratio of red pixels to green pixels and/or blue pixels in the image. The ratio of red to green pixels and/or blue pixels in the image is a linear function of the concentration of permethrin. In a preferred embodiment, the ratio of red to green plus blue pixels is determined for correlation with the amount of type I pyrethroid present in the textile object. In an embodiment, the signals produced by the red pixels and the green and/or blue pixels are digitized using any suitable program or application to provide quantitative data relating to the intensity of the orange/red color produced by the assay in the presence of a permethrin.

Digital imaging systems frequently utilize an RGB color model, which is an additive color model in which red, green, and blue light are added together in various ways to reproduce a broad array of colors. A Bayer filter mosaic is a color filter array for arranging red-green-blue (RGB) color filters on a square grid of photosensors. This particular arrangement of color filters is used in most single-chip digital image sensors used in digital cameras, video recorders, and scanners to create a color image. Typically, the filter pattern is composed of 50% green, 25% red, and 25% blue color filters.

The red pixels are sensitive to visible light having a wavelength of about 590 to 650 nm, while the green pixels are sensitive to visible light having a wavelength of about 495 to 570 nm and the blue pixels are sensitive to visible light having a wavelength of about 450 to 495 nm. The absorbance of the color produced in the inventive assay falls in the range of about 590 nm to about 650 nm. The green and/or blue pixels are used as a reference to normalize the response obtained. In another embodiment, the quantitation can be performed using reflective spectroscopy to monitor the absorbance/color intensity at a wavelength of about 590 to 650 nm.

In an embodiment, image analysis can be performed using a cell phone (e.g., a smartphone) equipped with a camera and image analysis applications.

The invention also provides a kit comprising (a) an absorbent substrate, (b) a solvent, (c) a solution of a nitrite salt in concentrated sulfuric acid, (d) at least one sample well, and (e) instructions for use. The absorbent substrate, solvent, solution comprising a nitrite salt, and sample well can be as described herein.

In an embodiment, the kit comprises (a) sample collection equipment to include a solvent applicator and an absorbent substrate, and (b) a colorimetric reaction container suitable for the placement of the absorbent substrate and solution comprising a nitrite salt. The solvent applicator can be any suitable solvent applicator and can be a spray bottle, aerosol spray container, sponge, or roller. The colorimetric reaction container can be any suitable colorimetric reaction container and can be an assay plate containing a plurality of sample wells, a culture dish, a beaker, Petri dish, or concave glass or plastic disk. Desirably, the colorimetric reaction container is inert to the solution comprising a nitrite salt.

In an embodiment, a chart depicting images of sample wells containing increasing known concentrations of type I pyrethroid after treatment with a solution of a nitrite salt can be prepared. Visual comparison of test samples with the standard chart allows for semi-quantitative analysis of type I pyrethroid levels in sample objects. The kit can further contain the chart.

In some embodiments, a standard calibrator disk containing an amount of a type I pyrethroid representing a "failed" textile sample is also added to the kit for comparison. The color intensity is compared to the standard calibrator disk for a "go/no go" assessment of type I pyrethroid content. The "failed" textile sample contains an ineffective amount of the type I pyrethroid to repel or kill insect vectors.

The following examples further illustrate the invention but, of course, should not be construed as in any way limiting its scope.

Example 1

This example demonstrates a colorimetric assay for measuring permethrin on treated military uniforms.

Fabric Sampling Procedure

The fabric to be tested is laid over a piece of solid plastic supporting material and a measured amount of solvent (e.g. acetone) is sprayed on the surface. Alternatively, a spongy porous material saturated with a solvent may be placed underneath the fabric.

A 10-mm glass fiber filter disk is placed on the wetted surface and pressed until it is saturated with the solvent containing dissolved permethrin from the fabric.

The disk is then air-dried.

Color Test

A 60×15 mm tissue culture dish is fashioned so that each well contains a matrix (2 sheets of glass fiber chromatography paper impregnated with silica) containing a premeasured amount (2 mL) of the colorimetric reagent (Liebermann Reagent), which is a 10% potassium or sodium nitrite in concentrated sulfuric acid. This method creates a reactive gel that eliminates handling of the caustic reagent and facilitates transportation without leakage.

The dried sample disk is placed into the wells and pressed firmly (e.g., via a glass vial) onto the matrix containing the colorimetric reagent. This technique allows for an immediate and consistent distribution of the reagent over the entire disk, resulting in an evenly distributed coloration. The orange/red color appears immediately and the color intensity is recorded via a camera for subsequent image analysis. Image analysis can also be performed using a smartphone equipped with image analysis applications.

Alternatively, a standard calibrator disk containing an amount of permethrin representing a "failed" uniform is also used for comparison. The color intensity is compared to the standard calibrator disk for a semi-quantitative assessment of permethrin content.

When the test is completed, the colorimetric reagent is neutralized by the addition of calcium carbonate and disposed.

Example 2

This example demonstrates the generation of a calibration curve that relates the ratio of red to green pixels in digital images of test samples to permethrin concentration.

Solutions comprising different concentrations of permethrin were treated with the Liebermann reagent in sample wells. Digital images were recorded of the sample wells. The images were analyzed to determine the ratio of red to green pixels, and a calibration curve generated. The calibration curve is depicted in FIG. 1. The correlation of the ratio of red to green pixels to permethrin concentration was found to be linear, and the response described by the formula: $y=0.5094x+0.7143$, with the correlation coefficient $R^2=0.9923$, wherein y=ratio of red to green pixels and x=permethrin concentration.

Example 3

This example demonstrates the selectivity of the assay, in accordance with an embodiment of the invention.

Sample glass fiber filter disks were treated with dibutyl phthalate, 3-phenoxybenzyl alcohol, deltamethrin, bendiocarb, and permethrin, and then subjected to the assay described in Example 1. A blank disk was included as a control. The disk containing permethrin was orange in color. The blank disk and the disk treated with dibutyl phthalate were colorless. The disk treated with 3-phenoxybenzyl alcohol was dark brown in color. The disk treated with deltramethrine was dark red in color. The disk treated with bendiocarb was light yellow in color.

Example 4

This example demonstrates the results of use of the assay in determining the levels of permethrin in permethrin-treated uniform jackets and pants.

Jackets and pants that were treated with permethrin in 2003, 2007, and 2012, as well as a factory-treated jacket and an untreated jacket as a control were subjected to the assay described in Example 1. Digital images of the samples after reaction with the Liebermann reagent were obtained, and the ratio of red to green pixels determined by image analysis software. The permethrin levels were determined using the calibration curve described in Example 2. The results are set forth in the Table.

TABLE

| Sample | Red to green pixel ratio | Permethrin ($\mu g/cm^2$) |
| --- | --- | --- |
| Pants treated 2012 | 1.2 | 0.95345 |
| Pants treated 2007 | 0.1 | ND* |
| Jacket treated 2012 | 5.9 | 10.1785 |
| Jacket treated 2007 | 0.4 | ND |
| Jacket treated 2003 | 0.9 | 0.3646 |
| Pants treated 2003 | 1.8 | 2.1313 |
| Factory-treated jacket | 3.9 | 6.2535 |
| Untreated jacket | 0.2 | ND* |

*ND = not detected

The variability in the results is a reflection of different amounts of permethrin used in producing the jackets and pants, as well as differences in amount of use and number of washings.

Example 5

This example demonstrates use of the colorimetric permethrin test to determine the depletion rate of permethrin in military uniforms as a function of washing frequency, in accordance with an embodiment of the invention.

Figure 2:
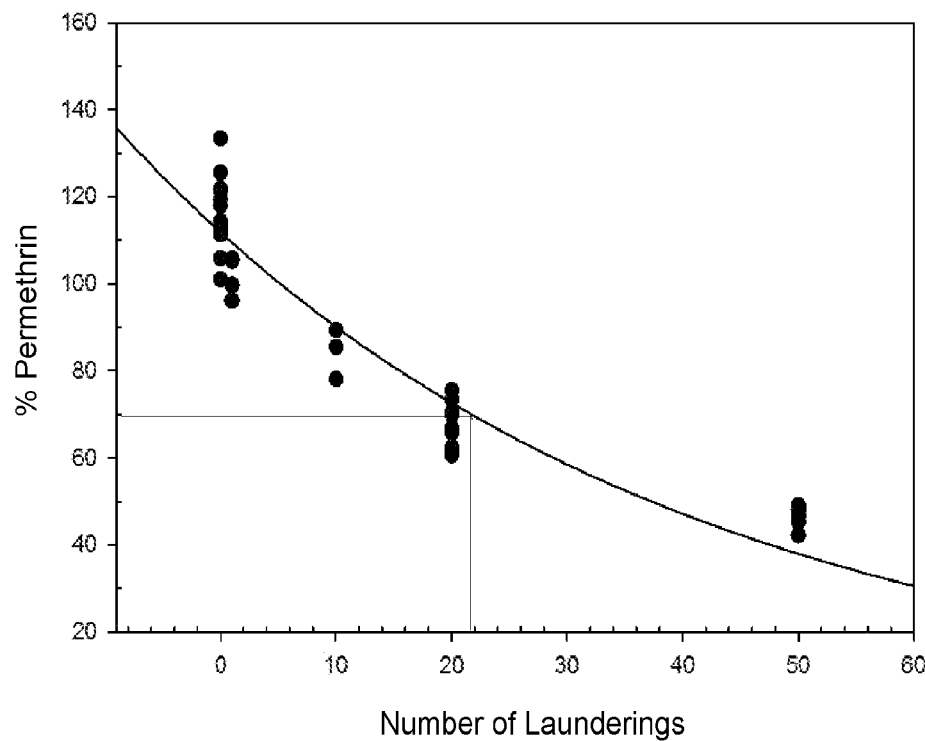
FIG. 2 depicts a graph of permethrin content of military uniforms as a function of the number of launderings.

Permethrin-treated military uniforms obtained from the same manufacturer and all belonging to the same lot were tested for permethrin content using the colorimetric assay described in Example 1. The uniforms were then laundered 50 times. The uniforms were tested for permethrin content after 10, 20, and 50 washings. The permethrin content of the uniforms was plotted graphically and a curve fitted to the data points. The graph is shown in FIG. 2. Use of the curve allowed for determination of the half life of permethrin in the uniforms, which was determined to be about 22 launderings.

No interferences were found to result from use of the washing detergents or from the flame-retardant chemicals used in these uniforms. Handling of the uniforms with bare hands did not contribute any residual substances that interfered with the assay.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for detecting a presence of a type I pyrethroid in an object comprising the steps of:
    (a) (i) contacting the object with a solvent and then contacting the object with an absorbent substrate or (ii) contacting the object with an absorbent substrate and then contacting the object with a solvent,
    (b) separating the absorbent substrate from the object,
    (c) evaporating the solvent from the absorbent substrate,
    (d) treating the absorbent substrate with a solution of a nitrite salt in concentrated sulfuric acid, and
    (e) observing the absorbent substrate for a color change, thereby detecting the presence of the type I pyrethroid in the object.

2. The method of claim 1, wherein the type I pyrethroid is permethrin.

3. The method of claim 1, wherein the solvent is acetone.

4. The method of claim 1, wherein the solution of a nitrite salt in concentrated sulfuric acid is a solution of sodium nitrite or potassium nitrite in concentrated sulfuric acid.

5. The method of claim 1, wherein the solution of a nitrite salt in concentrated sulfuric acid is contained within a sample well.

6. The method of claim 5, wherein the sample well further contains a carrier material, wherein the carrier material comprises glass fiber paper, wherein the carrier material and the solution of the nitrite salt in concentrated sulfuric acid form a matrix.

7. The method of claim 6, wherein the glass fiber paper further comprises silica.

8. The method of claim 1, wherein observing the color change comprises determining an intensity of the color produced by the color change.

9. The method of claim 8, wherein the intensity of the color produced by the color change is correlated with a concentration of permethrin in the object.

10. The method of claim 1, wherein the object is a textile.

11. The method of claim 10, wherein the textile is a military uniform or a mosquito net.

12. A kit for detecting a presence of a type I pyrethroid in an object comprising:
    (a) an absorbent substrate,
    (b) a solvent,
    (c) a solution comprising a nitrite salt in concentrated sulfuric acid,
    (d) at least one sample well, and
    (e) instructions for use comprising the steps of:
    (a') (i) contacting the object with the solvent and then contacting the object with the absorbent substrate or (II) contacting the object with the absorbent substrate and then contacting the object with the solvent,
    (b') separating the absorbent substrate from the object,
    (c') evaporating the solvent from the absorbent substrate,
    (d') treating the absorbent substrate with the solution of a nitrite salt in concentrated sulfuric acid, wherein the absorbent substrate and the solution comprising the nitrite salt in concentrated sulfuric acid are both contained within the at least one sample well, and
    (e') observing the absorbent substrate for a color change indicating the presence of the type I pyrethroid in the object.

13. The kit of claim 12, wherein the absorbent substrate comprises a glass fiber filter disk.

14. The kit of claim 12, wherein the solvent is acetone.

15. The kit of claim 12, wherein the nitrite salt is sodium nitrite or potassium nitrite.

16. The kit of claim 12, wherein the at least one sample well further comprises a carrier material.

17. The kit of claim 16, wherein the carrier material comprises glass fiber paper, wherein the carrier material and the solution of the nitrite salt in concentrated sulfuric acid form a matrix.

18. The kit of claim 17, wherein the glass fiber paper further comprises silica.

19. The kit of claim 12, wherein the kit further comprises a visual correlation chart, wherein the visual correlation chart depicts images of sample wells containing increasing known concentrations of type I pyrethroid after treatment with a solution of a nitrite salt, wherein the visual correlation chart allows for semi-quantitative determination of type I pyrethroid concentrations in a sample via visual comparison of the absorbent substrate in step (e') with the visual correlation chart.

20. The kit of claim 12, wherein the kit further comprises a standard calibrator disk, wherein the standard calibrator disk contains an ineffective amount of the type I pyrethroid to repel or kill insect vectors.

* * * * *